(12) United States Patent
Voegeli et al.

(10) Patent No.: US 8,961,873 B2
(45) Date of Patent: Feb. 24, 2015

(54) ANTINFECTION PROTECTING HEALTHCARE WORKERS TO PREVENT SPREADING OF COMMUNICABLE AND NOSOCOMIAL INFECTIONS

(76) Inventors: Fridolin Voegeli, Thalwil (CH); Ghanem E. Ghanem, Drogenbos (BE)

( * ) Notice: Subject to any disclaimer, the term of this patent is extended or adjusted under 35 U.S.C. 154(b) by 0 days.

(21) Appl. No.: 13/983,639

(22) PCT Filed: Feb. 2, 2012

(86) PCT No.: PCT/IB2012/000179
§ 371 (c)(1),
(2), (4) Date: Aug. 5, 2013

(87) PCT Pub. No.: WO2012/104718
PCT Pub. Date: Aug. 9, 2012

(65) Prior Publication Data
US 2013/0309128 A1 Nov. 21, 2013

Related U.S. Application Data

(60) Provisional application No. 61/439,395, filed on Feb. 4, 2011, provisional application No. 61/524,904, filed on Aug. 18, 2011.

(51) Int. Cl.
*A61L 2/00* (2006.01)
*A61K 51/00* (2006.01)
(Continued)

(52) U.S. Cl.
CPC .................. *A61L 2/0088* (2013.01); *A61L 2/22* (2013.01); *A61L 2202/14* (2013.01); *A61L 2202/15* (2013.01)
USPC ..................... 422/28; 422/1; 422/37; 424/1.8; 424/78.25; 424/76.8; 424/78.07; 514/2.3; 514/759; 252/186.36; 252/187.1; 252/380

(58) Field of Classification Search
CPC ........ A01N 1/0215; A61K 8/315; A61L 2/00; C09D 127/12
USPC ............. 422/1, 28, 37; 424/1.8, 78.25, 78.07, 424/76.8, 632; 514/2.3, 759; 252/186.36, 252/187.1, 380
See application file for complete search history.

(56) References Cited

U.S. PATENT DOCUMENTS

| | | | |
|---|---|---|---|
| 4,374,126 | A | 2/1983 | Cardarelli et al. |
| 5,512,199 | A | 4/1996 | Khan et al. |

(Continued)

OTHER PUBLICATIONS

Sax et al., 'My Five Moments For Hand Hygiene': A User-Centered Design Approach to Understand, Train, Monitor And Report Hand Hygiene, Journal Of Hospital Infection, 2007, 67, pp. 9-21.

(Continued)

*Primary Examiner* — Monzer R Chorbaji
(74) *Attorney, Agent, or Firm* — Gifford, Krass, Sprinkle, Anderson & Citkowski, P.C.

(57) ABSTRACT

The present invention describes a new system and method, named "Antinfection", to protect primarily healthcare workers (HCWs) and patients against communicable and nosocomial infections. It's based on new antiseptic sprays, non-alcoholic, that can be sprayed automatically on the hands. The base of the antiseptic action is the persistent part, preventing the colonization of tissue and non-living surfaces with microorganisms through the targeted, on-demand release of Fluorine ions. The system including new sprayers for fast and controlled application; new technologies to secure the long-term protection against wear in the daily work routines of HCWs; new measurement techniques for the quality of the Antinfection; new quality recording concepts for the promotion and verification of new strategies and campaigns in the "lost war against the germs".

20 Claims, 4 Drawing Sheets

(51) Int. Cl.
   *A61K 31/79*   (2006.01)
   *A01N 29/02*   (2006.01)
   *C09K 3/00*    (2006.01)
   *A61L 2/22*    (2006.01)

(56) References Cited

U.S. PATENT DOCUMENTS

| | | | |
|---|---|---|---|
| 7,488,757 B2 | 2/2009 | Hoang et al. | |
| 8,445,030 B2 * | 5/2013 | Voegeli et al. | 424/675 |
| 2010/0312201 A1 | 12/2010 | Hoege | |

OTHER PUBLICATIONS

Wallhäussers "Praxis der Sterillstion, Desinfektion, Antiseptik und Konservierung" Qualitätssicherung der Hygiene in Industrie, Pharmazie und Medizin, Chapter 7, pp. 146-160.

Wallhäussers "Praxis der Sterillstion, Desinfektion, Antiseptik und Konservierung" Qualitätssicherung der Hygiene in Industrie, Pharmazie und Medizin, Chapter 8.6, pp. 212-219.

World Health Organization, WHO Guidelines On Hand Hygiene In Health Care: A Summary, WHO/IER/PSP/2009.07, pp. 1-52.

* cited by examiner

Figure 1:
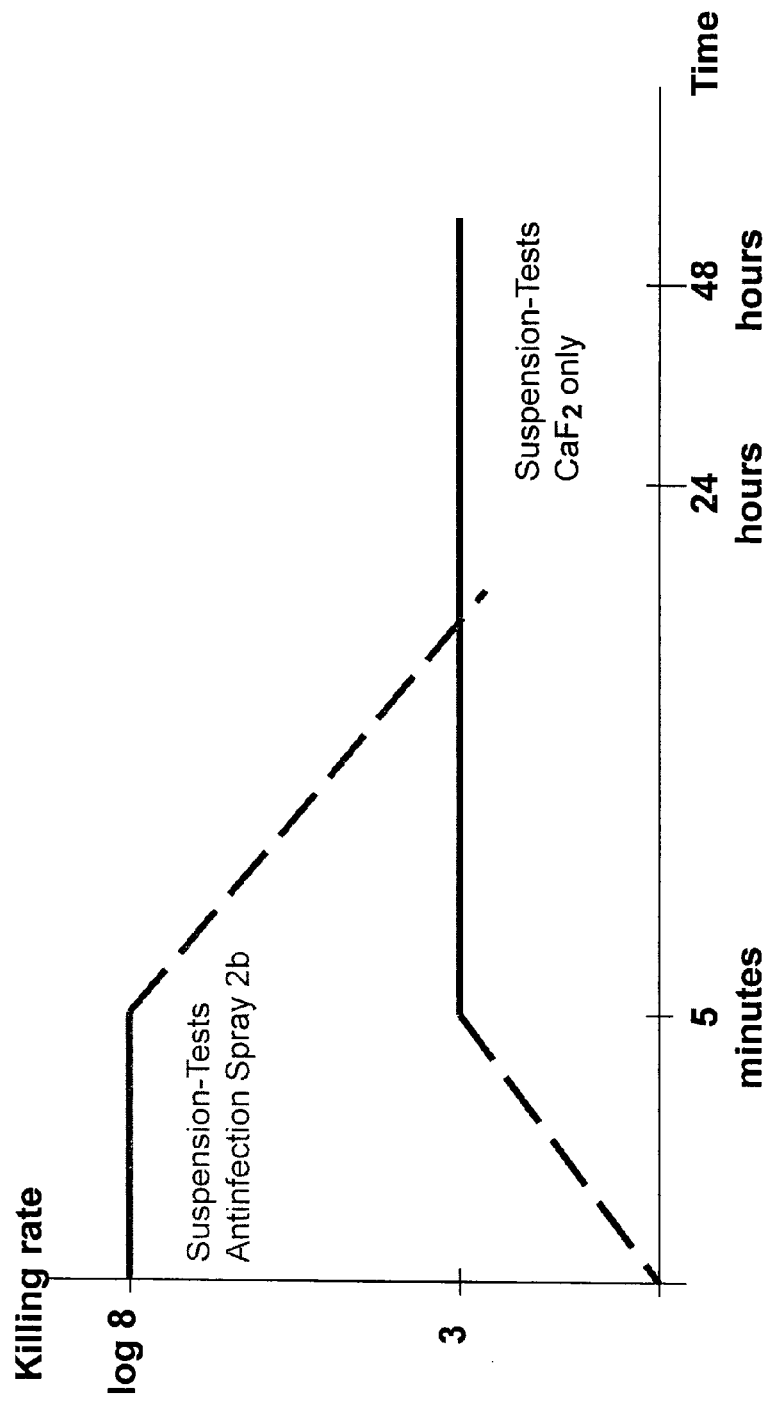

Fig 1. Efficacy/Time for MedoSept Antinfection Spray 2b

ANTINFECTION PROTECTING HEALTHCARE WORKERS TO PREVENT SPREADING OF COMMUNICABLE AND NOSOCOMIAL INFECTIONS

CROSS-REFERENCE TO RELATED APPLICATIONS

Application PCT/IB2012/000179 claims the benefit of U.S. Provisional Application 61/439,395 filed on Feb. 4, 2011. Application PCT/IB2012/000179 claims the benefit of U.S. Provisional Application 61/524,904 filed on Aug. 18, 2011.

FIELD OF THE INVENTIONS

The present inventions relate to new concepts and practices of "Antinfection" to protect primarily healthcare workers (HCWs) and patients against communicable and nosocomial infections; including new Antinfection Sprays with long-term efficacy; new sprayers for fast and controlled application; new technologies to secure long-term protection against wear in daily work routines of HCWs; new measurement techniques for the quality of Antinfection; new quality recording concepts for promotion and verification of new strategies and campaigns in the "lost war against the germs".

BACKGROUND OF THE INVENTIONS

Antiseptics are antimicrobial chemical substances applied to living tissue/skin to reduce possibility of infection, sepsis or putrefaction caused by microorganisms. Disinfectants destroy microorganisms found on non-living objects.

In the second half of the nineteenth century, inspired by Louis Pasteur's germ theory of diseases, doctors Lister, Semmelweis, Tichenor and others introduced antiseptic treatment and surgical methods into their daily work, and initiated a completely new quality of medicine: Open wounds, surgery and infectious diseases no longer led to painful death, but where banned through topical antiseptics, and cured later by internal antibiotics.

From the beginning Pasteur and his followers stipulated that disinfection and antiseptic methods are not 100% effective procedures and have to be verified and classified using the "killing rate" on specific microorganisms reached and attacked by disinfecting agents. Today we apply "fast acting" and "persistent" topical antiseptics, that all should be "broad spectrum", i.e. effective against a variety of microorganisms.

Fast acting antiseptics are measured by significant reduction in "colony forming units" (CFU) found on cultures obtained some minutes following application of antiseptics. The quality of "persistence" refers to the ability of an antiseptic, to continue to kill germs, once it has been applied to the skin, and is due to retention or binding of chemicals on the skin, after partial evaporation and after rinsing.

Many powerful and fast acting antiseptics have been developed by chemists and applied by doctors and households. Some have been abandoned, because they produced side-effects, others because they where just too inexpensive and not sufficiently profitable to medical industry: A handful, mainly "alcohol-based-hand-rubs" (ABHR), became "gold standards".

DESCRIPTION OF PRIOR ART

After World War II and the invention of antibiotics, the "war against the germs" through hand hygiene became one of the main tasks of new national CDCs (Communicable Diseases Centers) and the global acting WHO (World Health Organization).

But "persistence", state-of-technology in food industry, in water supply and in ancient embalming practices, remained an elusive goal for medical antiseptic technology, up to these days. Regulating bodies like the FDA have required persistence since the 1970s for any new antiseptic to be approved; with very little response, actually monopolizing utilization of outdated, non-persistent, alcohol-based disinfectants. Additional regulations in Europe, for new antiseptics to be tested and evaluated as "medications", in lengthy and costly clinical trials, led to an end to all small enterprise chemical development and production of novel disinfectants.

In the 1970s new infectious diseases, like HIV caused AIDS, entered the theater. This time, infected people were no more isolated from public, and "discriminated", but were allowed to move "more than freely" and spread the deadly viruses. Instead of preventing this proliferation at the source, the receivers were asked to offer to the infected people every "right for highest level health care".

In 1990, for the first time, CDC reported a possible transmission of HIV from a dentist to a patient in Florida during an invasive procedure, and a few months later same was reported from a surgery in a European hospital. This was the starting point for at first amazing guidelines that turned later into terrifying statutory regulations in health care facilities: All HCWs were forced now to clean (=des-infect) their hands, instruments and installations, before each patient and after each patient, in order to "evidently guarantee" to the patient, that he will not be infected by the doctors and their care.

A "patient-centric model" was created and promoted: All hands that might touch the patient should be cleansed, before contact and after contact. "Clean Hands are Safe" and "Clean Care is Safer Care" became new slogans of WHO.

A "Patient Zone" was defined around the patient's bed in the hospital room or around the patient's chair in the doctor's office. All persons approaching this Patient Zone had to have clean, des-infected hands, in order not to deliver new germs to the (infected !) patient. And after working on him they all had to clean (=des-infect) their hands again, not to carry any germs away to another Patient Zone.

The latest best-practice (after 2003) was called "My five moments for hand hygiene":

1 before patient contact
2 before aseptic work
3 after body fluid exposure
4 after patient contact
5 after contacts with patient surroundings In the opinion-leaders' *Journal of Hospital Infection* (2007) the experts summarized their recommendations:

Hand hygiene as it is understood today requires three to 30 applications of hand rub per hour during patient care which translates to one hand rub every 2 min during intensive care activities. (and they continue: The reality, however, is that unobserved HCWs only perform very few hand hygiene actions during their work day . . . ).

These required best practices of hygiene have been criticized as perverted by most doctors, because:

All these cleaning activities are centered around an un-cleaned, 100%-certainly infected patient. The same patient, who e.g. had just entered the doctor's clinic a half hour ago, with flowing nose and feverish eyes, directly from the street, with dirty hands and sneezing. He was not asked to clean himself, but went straight to the waiting room, were he shook hands with two old comrades, apparently also flue-infected, grabbed one of worn-out magazines, licked his fingers and opened it; after 10 minutes he went to men's room and came back without washing his hands; after another 5 minutes he had a sneeze-attack for about 20 seconds and used his old handkerchief extensively; before being called into doctor's room to check for 30-60 seconds how "his doctor cleans the hands for clean care". This happens 40-50 times a day in a general practitioner's office, the doctor losing at least 1-2 hours precious time every day, and his personal health, with alcohol-based-hand-rubs.

The inventor's wife works in a school-clinic as an orthodontist, suffering the whole year from allergies caused by highly toxic disinfectants prescribed by government agencies, plus in the winter half-year suffering from infections caught from the young patients: Most of these lower-class children need orthodontic corrections because they did not treat their first teeth correctly and are regularly thick with flue in fall and winter. Before each new patient, the doctor has to open windows, spray the whole room, clean and des-infect all surfaces in reach of the patient, exchange his instruments, change to new gloves and des-infect his hands in between, put on a new face mask and cap, etc. Just to look into the mouth of his new patient, who came in from the street, has not disinfected his hands, has not cleaned his face nor gurgled with some antiseptic mouth-wash; and with the first high-speed drill spills millions of his bacteria over the doctors "cleaned" face.

Nature has produced the bill for these contra-productive des-infection concepts, as can be read in the foreword to the latest of campaigns promoted by the WHO (2009):

Healthcare-associated infections affect hundreds of millions of patients worldwide every year. Infections lead to more serious illness, prolong hospital stays, induce long-term disabilities, add high costs to patients and their families, contribute to a massive, additional financial burden on the healthcare system and, critically, often result in tragic loss of life . . . .

US Medicare in 2004 analyzed the cost explosion in hospital care:

Almost one fifth (19.6%) of the 11,855,702 Medicare beneficiaries who had been discharged from a hospital were re-hospitalized within 30 days, and 34.0% were re-hospitalized within 90 days; 67.1% of patients who had been discharged with medical conditions and 51.5% of those who had been discharged after surgical procedures were re-hospitalized or died within the first year after discharge . . . . We estimate that the cost to Medicare of unplanned rehospitalizations in 2004 was $17.4 billion.

Let's summarize the result of prior art in hand disinfection: For 100s of millions (N) of patients each (N) year disinfection came in too late and was not effective. The patients came down with life-threatening infection diseases, had to be treated with antibiotics and generated tremendous cost.

For some 10s of millions (!!) of patients each (!!) year also antibiotics came in too late and were not effective. The patients died an agonizing death, in spite of exorbitant cost. For some 100s of millions (!!) of patients next (!!) year the efficiently communicating bacteria have already developed some new tricks to make different variants of antibiotics ineffective, much faster then we can develop new ones. Next year even more patients will die off and very soon we shall no more have unspent antibiotics.

There are many things basically wrong with these present-days des-infection practices; with the "post-infection" application, missing preventive and persistent technologies; with the way these fervent ABHRs are "sponsored" by big industries and enforced by government authorities; and with the alarming extent to which they are avoided by frustrated doctors and hurt HCWs.

SUMMARY OF THE INVENTION

In an innovative bottom-up approach, actual methods and means have been analyzed and new solutions have been invented and designed for a paradigm change:

1. "Antinfection Practice" was designed as new best practice, protecting the hands (and other eventually exposed body parts) of doctors, HCWs and patients, before infection, preventing new contamination through transmission from and to patients and objects, preventing (auto-) colonization trough killing and suppressing re-growth of resistant species; guaranteeing "best Antinfection time" for hours in daily work routine.

The German version of Wikipedia teaches us about the skin to be protected:

Healthy skin is heavily colonized by microorganisms, most bacteria and fungi, building as commensals or mutuals a natural superficial layer on the skin surface, named skin flora. They offer one important benefit in defending the skin and the organism as a whole against pathogen germs and form part of the microbiom.

As long as the skin, barrier-organ to the environment, remains intact and executes its barrier function, commensales and mutuals do not cause irritations, do not generate diseases and act for many reasons quite beneficial. At the microscopic level of the skin surface, the non pathogen commensals defend their territory very aggressively. If some new germs want to enter into the body, they first have to battle with these "doormen". Only new germs that can overcome the "resistant flora", can invade deeper.

In addition the resident mutualistic germs produce metabolites beneficial for skin integrity . . . .

. . . The numbers of resident microorganisms range from $10^2$ to $10^6$ per $cm^2$ on the different body areas: finger-tips 20-100, hand $10^3$, dorsal $3\times10^2$, feet $10^2$-$10^3$, forearms $10^2$-$5\times10^3$, forehead $2\times10^5$, scalp $10^6$, armpit $2\times10^6$ (all per $cm^2$). In total some $10^{10}$ bacteria live on our 2 square meter of body surface, some $10^{12}$ (99% !!) inside the body.

Antinfection Practice therefore has the goal to protect the resident skin flora from contamination and colonization by transient germs and to suppress auto-colonization and auto-infection by re-growth of own pathogen germs that have been under control in the microbiome during healthy skin.

Antinfection Practice is not focusing on des-infecting the HCW's hands x-times a day, destroying all skin flora and depleting the skin from all its natural protection, in order to not transmit any germs to the already infected patient in the Patient Zone of his hospital bed or doctor's chair.

In contrary: in Antinfection Practice the medical facility is divided into different, defined "Antinfection Zones", based on the tasks HCWs have to perform therein.

All actors entering the Antinfection Zone, most important patients and visitors (!), shall wash, protect and cover their hands and other eventually exposed body parts with Antinfection Spray, protecting themselves for the whole time of their planned stay. All hands shall be protected and there shall be no more any import of germs, and export of germs, even if hands may come into contact with eventually contaminated patient skin, fluids or patient surroundings. Inside the Antinfection Zone, infrastructure and resident patients shall be checked regularly for safe "Antinfection Time" and shall be re-protected for required prolonged duration of stay.

First goal is, to protect the HCWs: They will no more play their "central role as the main transmitter of germs" from unprotected patient bodies to unprotected HCWs hands and to next patients, because all these hands and next patient's skin are no more cleansed and defenseless, but persistently covered and protected for the whole time in the Zone.

Figure 3:
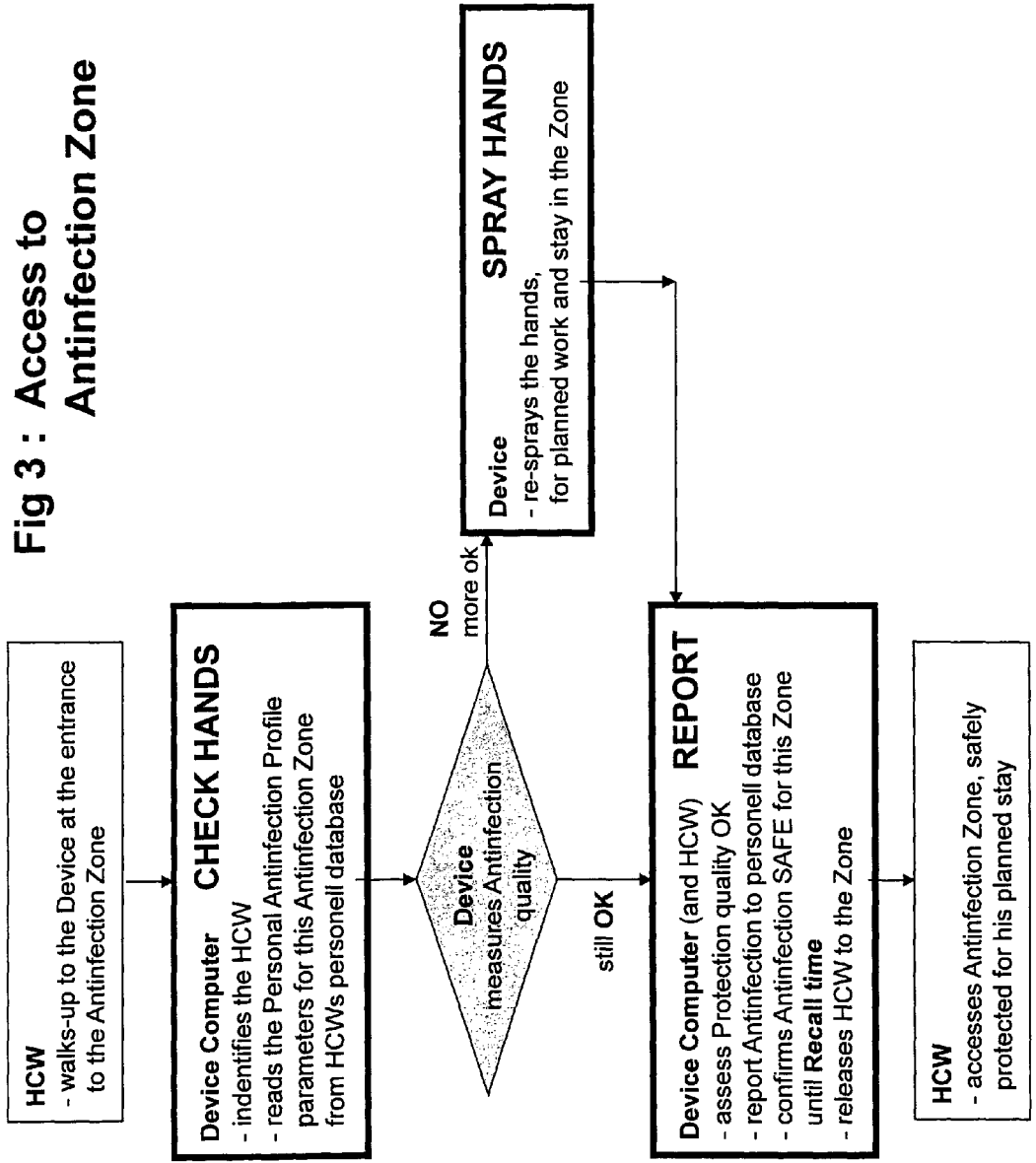
Figure 4:
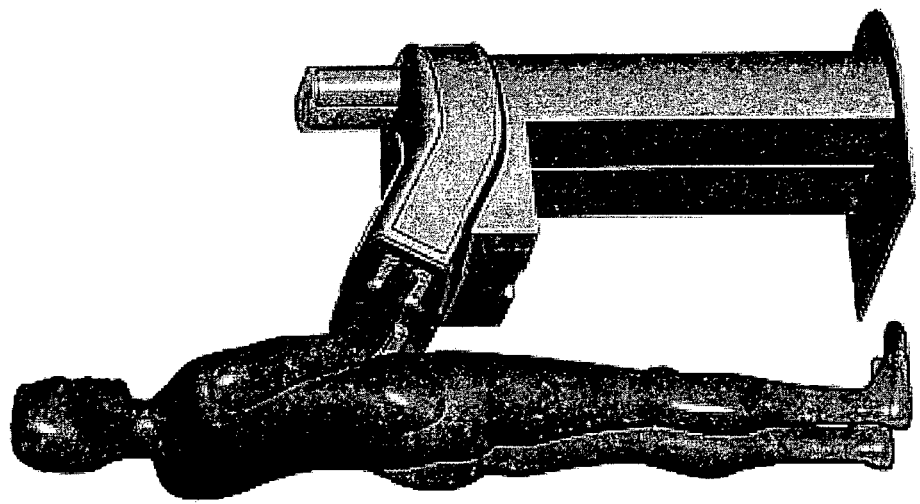

FIG. 3 shows the new procedure of "Access to Antinfection Zone", with the 3 phases: "CHECK HANDS", "SPRAY HANDS", "REPORT".

In CHECK-HANDS at a new Antinfection Zone, the HCW will have his remaining Antinfection Time on his hands evaluated and confirmed by the Device computer before entrance. The Computer also identifies the HCW, reads his work-profile for this Zone. If his remaining Antinfection Time is shorter than the planned stay (according to HCW's work profile), the Device will automatically "re-SPRAY HANDS" and will re-confirm renewed Antinfection Time, REPORT it to database and to the HCW, as a recall-limit.

2. "Persistent and fast acting Antiseptics and Disinfectants based on Calcium-Fluoride" have been designed, based on natural fine minerals that can act as persistent "Antinfection Coatings" and can prevent microorganisms to colonize skin tissue and non-living surfaces for hours and days, while maintaining and eventually enforcing skin's natural protection flora and protection mechanisms. Fast acting acids from plants and fruits were added in highest feasible saturation to act fast in the beginning of Antinfection procedure or at new contact with patient's body fluid. This invention has been filed as U.S. patent application Ser. No. 12/882,296.

FIG. 1 shows resulting, measured efficacy/time diagram of sample Antinfection Spray (composition see Table I): Fast acting plant acids kill within 30 sec with log 8 to 9 (=thousand times stronger than alcohol-based-hand-rubs!) any free germs on skin surface. And any later arriving germs, from contact with the patient and his surroundings, will be killed while landing on a deadly $CaF_2$-coating. Transmissions of germs are blocked, for hours and days, in particular proliferation from HCW to patients.

These new Antinfection Sprays are water-based, non-toxic, non-alcoholic, non-explosive, non-irritating, non-cauterizing, etc. This combination of high, persistent efficacy and very low risk and hazard for user and environment, enabled all the follow-up developments and inventions, described below.

TABLE I

Formulation $CaF_2$-based Antinfection Spray
[mg/litre antiseptic molecules/droplet]

| Pure water | 980 g | (98%) | |
|---|---|---|---|
| $CaF_2$ | 50 mg | $2.5 \times 10^{10}$ | extreme long-term antiseptic |
| Organic acids | 1500 mg | $50 \times 10^{10}$ | fast acting, short-term |
| Organic salts | 2500 mg | $250 \times 10^{10}$ | fast acting, medium-term |
| Alginate | na | | |

2b. New "Spray-on Matrix" was designed, covering skin and skin flora plus securing the Antinfection Reservoir against mechanical abrasion and washing-off, preventing germs to get thru its wired entanglement, enabling delayed but fast release of $CaF_2$ and other long-term active molecules against new arriving colonization.

Figure 2:
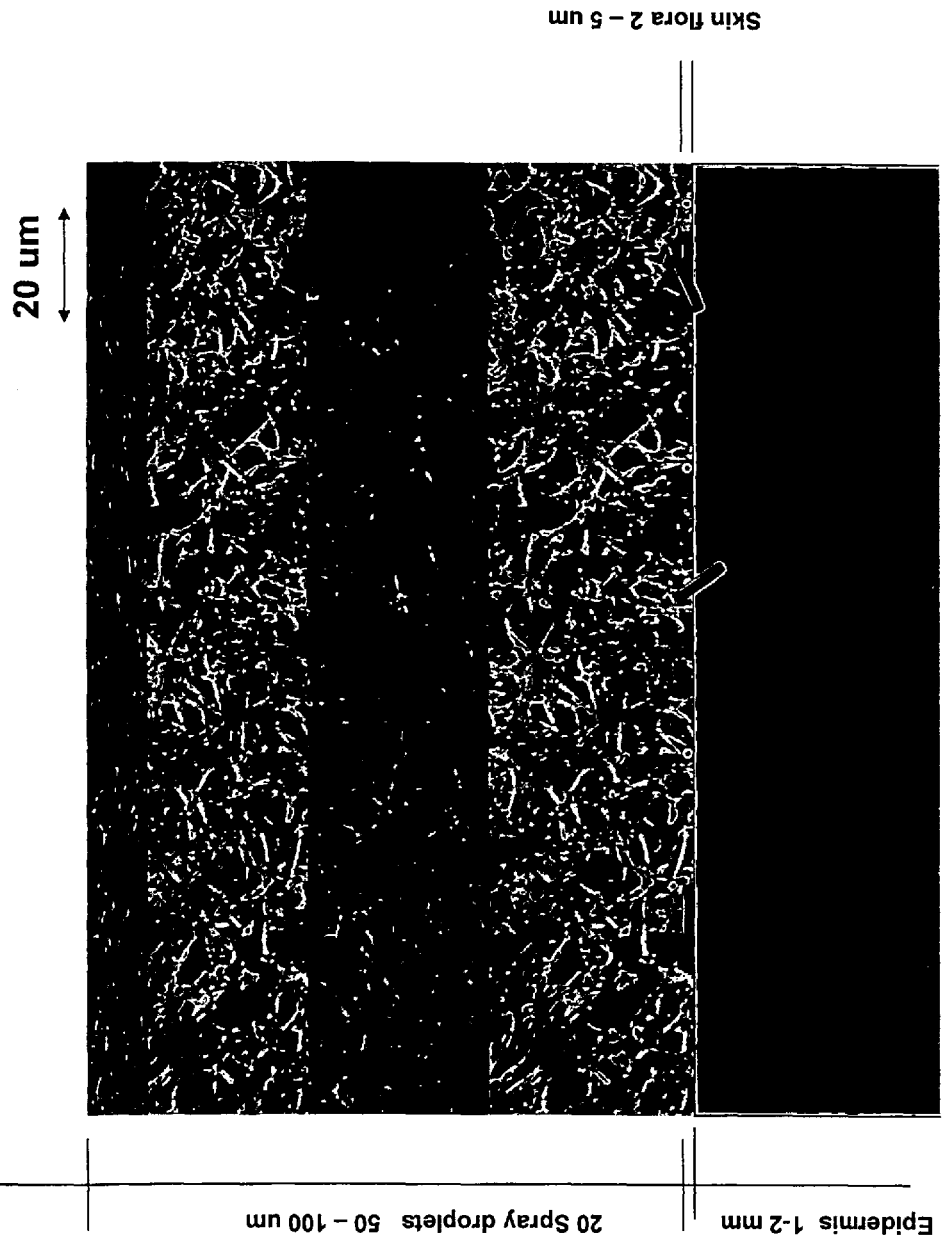

FIG. 2 gives a sectional view at the microscopic level on the hand surface of a HCW:

On the washed and dried epidermis of 1 cm² (>1 mm thick) one can find some $10^3$ germs, covering <1% of the surface. Some $150 \times 10^3$ water droplets are sprayed on the cm², some 150 on top of each germ's territory, 3 layers high (some 0.1 mm). Each of the droplets contains some $5 \times 10^{12}$ antiseptic molecules and some $10^{10}$ very long polymer molecule threads. The droplets are pressed against the skin with hot air and dried out. When the germ recovers from the first shock it is immobilized by a matrix of some $4 \times 10^{12}$ fibers. In this entanglement some $500 \times 10^{12}$ antiseptic molecules are waiting for a movement of the germ, to touch and kill it and to compete for any rest of water or new sweat or other fluid, to re-start reproduction and auto-colonization.

NO germ from the inner resident flora can leave the skin surface and contaminate other objects, NO germ from other donors can land on the outer surface without being trapped in the entanglement and killed by reservoir molecules.

FIG. 1 plots the long-term activity of a $CaF_2$-based Antinfection Spray on HCWs at doctor's office, who seldom do heavy and wearisome care on patients. For the heavy workload of intensive care, or in assisted living care at patients' homes, with patient lifting and dressing, with aseptic work and patient washing, with contacting (body) fluids, etc. additional covering of protected hands is needed, obtained with rubber gloves over the des-infected hands, as required in actual surgical hand hygiene or with textile gloves also covered with Antinfection Spray.

Hands are safe in rubber gloves, because and as long as these are airtight. But transmission from infected patient to surroundings or to next patient is not interrupted; gloves therefore have to be changed or disinfected after (or before?) each patient.

In the Antinfection Zone no transmissions take place, because all hands and objects are protected with persistent antiseptic coating. The structure of this coating does not have to be airtight, in contrary, it has to release additional killing agent from "built-in reservoir" in the coating on new invaders and has to absorb the few survivors into some blocking hideaway. The covering matrix has to be stringy and viscous to protect skin and the built-in reservoir from abrasion and washing-off; just like the old-fashioned "car wash sponge" we all used, that also released soap from an inside pocket, when ever we pressed the sponge or we flushed more water through it.

Based on above requirements, specific polymers have been designed and mixed. They are applied within the antiseptic spray or in a second, polymers-only-spray. The giant molecules of the polymers,—molecular weight of over 40'000—, build long "threads" that cross-link on surfaces of skin, devices and instruments, when the water dries of, and build a sponge-like structure. (In industry similar polymers are applied in surface paints and wall coatings that have to stay and adhere for years; and are even mixed directly into injection plastics).

The density of the matrix can be programmed, adding more or less polymer in the water. It generates a heavily immobilizing surface for germs that have to crawl over and through large barbed-wire obstacles and get trapped in edged fence holes, while being exposed to attacking fluorine ions. And all over the long body of these polymer molecules there are electrically charged groups that cling around germs like tentacles and crack their cell membranes: Polymers can act as some best broad-spectrum biocides.

3. A "Device for Applying a Fluid to a Body Part" was designed, offering to user a closed internal spray chamber with multiple and moving nozzles and automatic control of spray process. Nozzles were multiple and moving relative to the inserted, stabilized hand, in order to direct spray onto 100% of hand surface and perform 100% wetting. This invention has been granted German Patent Nr DE 102007058180, has been filed as PCT Patent Application Nr WO 2009/071641, as European Patent Application Nr EP 2231340 and is pending as US Patent Application Nr US 2010312201.

FIG. 3 shows a user inserting his hands into Antinfection Device to get Antinfection protection.

3b. New Electrostatic Spraying techniques were developed and implemented that allow fast and verified, 100% wetting of the hands.

Efficacy of any protection in new Antinfection and in old-type hand des-infection, can be measured in numbers of "colony forming units" (CFU) of germs killed, and is the product of 4 independent factors:
factor 1: % wetting of skin surface
factor 2: killing rate of the spray on wetted skin surface ("log")
factor 3: time duration of killing
factor 4: ease of assessment, i.e. of correction and improvement
Final protection=factor 1×factor2×factor3×factor4.

In actual manual alcohol-based-hand-rub (ABHR) practice,
wetting of skin surfaces will always be less than 100%; with 2.5 milliliters for each hand and immediate start of evaporation, we estimate some 98% maximum;
killing rate of fast-acting agent on remaining wetted surfaces is around log 4-5, depending on "contamination load" to be eliminated;
time duration of killing activity is some 30-60 seconds; after this time alcohols have evaporated and there is no more killing for the remaining 60 seconds to next recommended (but avoided) cleaning action;
there is no measurement or assessment of quality of above des-infection factors that would enable the user to correct his insufficient cleaning before des-infection, his inefficient technique for wetting, or his too short rubbing efforts.

If today's maximum manual wetting of hand surfaces was less than 98%, and was evaporated after some 30-60 seconds, then the overall efficacy of des-infection was always less than log 2 (!); i.e. less than all data-sheets promised, and definitely less than all biocidal product requirements! And less than frustrated hospital owners expected.
Experts in biochemistry state: "Today's des-infection using alcohol-based-hand-rubs facilitates breeding of resistant germs through positive selection."

Electrostatic spraying technology, widely used in painting industry and in food conservation, was re-designed and applied to the human skin. From multiple nozzles, negatively charged droplets are directed to free, positively charged skin parts, until 100% of the skin is covered with negatively charged large molecules adhering to skin and immobilized bacteria, eventually killing them through electric charge and concentration gradients. Spraying duration is less than 2 seconds and spray used is less than 5 milliliters total for both hands.

This spraying technique has also been adapted and proofed successful in full-body Antinfection: Within some 5 seconds a person is fully protected and will not bring any external germs into the Antinfection Zone of a hospital or outpatient facility. (In countries where hospitals do more full-body washing on incoming patients, like in the Netherlands and Denmark, rate of nosocomial infections is 10-50 (!) times lower than in high-medtech Germany, where patients and visitors enter medical facilities without disinfection).

Above described new Antinfection Sprays, water-based, non-toxic, non-alcoholic, non-explosive, non-irritating, non-cauterizing, etc. allow for application of electrostatic spraying techniques; alcohol-based solutions can not be sprayed.

3c. Alternatively new air-pressure system was invented to evenly and 100% cover the surface of the hands with the sprayed-on fluid.

There will be many settings where application of above described electrostatic spraying techniques will not be accepted or technically cleared. An alternative solution to reach even, guaranteed 100% wetting and coating on the hands was designed: Frequently used in public and healthcare hygiene are Hand-Dryers that use high-pressure air from multiple vents or slits to wipe-off the water from the washed hands, down into a semi-closed collecting bowl. Mitsubishi first introduced these machines into public conveniences, Dyson copied the idea and markets them now also, slightly modified (see GB 2428569 Patent Application).

The concept of the high-pressure wiper has been kept for the "first pass", drying the washed hands. In a second pass the hands are sprayed from lateral nozzles, on the move down into the cavity, and when pulled up and out again, reduced air-pressure is smoothing the fluid onto the whole surface, especially to the furthest down finger-tips that need the thickest coating against abrasion in working.

If the lower pressure air is hot, it not only speeds-up the drying process but also boost the first short-term action of different compounds in the Antinfection Spray.

4. User identification was installed enabling qualified users to be optimally protected through "Personal Antinfection Profile" and "Personal Assessment".

Present-day legislation requires full accountability and documentation of compliance of all disinfection activities: Doctors have to keep record of all disinfections done in their office, on patients and assistants, including time stamp. Hospitals have to install RFID person identification to monitor all sprayings done over the day and to refer them to the single HCW; just to make sure that any future case of nosocomial infection can be traced back to the last little HCW; what for?

In the Antinfection Device automatic control of "applying fluid to a body part" is done by an embedded computer, with camera sensors assessing hands position and quality of spraying, and identifying persons passing by and users doing Antinfection. Iris signature, as used in Navy's security settings for admission control, has been improved to identify the user within the 1-1.5 seconds of his CHECK HANDS on the Device. (With this, computer not only reports the user and his activity; it also checks if this user has rights to access this Antinfection Zone, checks if there are messages waiting for him, etc.)

Computer systems in the Antinfection Device get the user's "Antinfection Profile": Type of work he shall do; how long his protection must be safe; when he needs to do a complete new Antinfection procedure; when he only needs a fresh-up procedure; if he is a hairy type and needs more spray, etc. Computers show to the user his hands in the spray chamber and the remaining coating, show him if a new spraying is required and how it is done, and guarantee to him that he is really SAFE for the requested hours, in his personal routine or ordered special work, within this Antinfection Zone.

4b. New Quality measurement and Quality reporting was implemented, in order to collect the basic data for local improvements of Antinfection practice, and for build-up of (global) Best Practice Knowledge-bases, to finally optimize strategies in the "war against the germs", based on solid evidence.

Direct measurement technology for "Antinfection Quality" has been developed:

In a first step, in-vitro and in-vivo, assumption was proven, that long-term antiseptic efficacy can be exactly quantified counting free negative ions from fluorine and other halogens in the coating. Only 16 ppm of CaF2 go into solution in water, the rest will remain in inactive suspension, waiting for free ions to be consumed by new contamination load. Long-term availability of such free ions has been sampled from hands and verified in cultures.

Applying fluorescence measurement, image analysis software can evaluate the amount of coating on the skin: if the coating still contains enough suspended halogen crystals to strike off and balance completely new colonization efforts.

Quality of coating on HCWs hands can be measured when entering Antinfection Zones and when leaving. The system may also ask qualified users about some specific parameters and results of work just performed.

All Antinfection Devices are connected to the Internet and shall REPORT these measurements to some teleservice centers: Quality of operation, usage and automatic resupply, maintenance and inspections, error operation and attempted vandalism, etc.

But even more important, medically relevant information about success and problems of this protection against germs invasion is REPORTed and stored on the Net, adding to knowledge available for medical and hygiene experts.

REFERENCES

Wallhäussers "Praxis der Sterilisation, Desinfektion, Antiseptik and Konservierung", Kramer, Assadian, et al, 2008.

"WHO Guidelines on Hand Hygiene in Health Care: a Summary", WHO, 2009.

'My five moments for hand hygiene': a user-centered design approach to understand, train, monitor and report hand hygiene", Sax et al, Journal of Hospital Infection, 2007.

U.S. patent application Ser. No. 12/882,296: "Persistent and fast acting Antiseptics and Disinfectants based on Calcium-Fluoride".

US Patent Application No 2010312201: "Device for Applying a Fluid to a Body Part".

U.S. Pat. No. 7,488,757: "Invisible Antimicrobial Glove and Hand Antiseptic", Hoang et Hunt, March/2004.

U.S. Pat. No. 5,512,199: "Hand Wipe Solution", Khan et Hoang, November/1993

U.S. Pat. No. 4,374,126: "Film Forming Antimicrobial Material", Cardarelli et Evans, February/1981

What is claimed:

1. A method of controlling the spread of infectious diseases between two contiguous areas of a facility by personnel passing through a portal connecting the two areas, comprising:

subjecting, at the portal, at least certain of the exposed body parts of the personnel with a high persistence antiseptic skin coating;

subjecting said certain exposed body parts of the personnel with a sprayed coating matrix of polymers;

measuring the antiseptic strength of the coatings based on their suspended halogens to evaluate the effective time of antiseptic protection afforded by the coatings; and storing a record of the identity of the person subjected to the coatings and the time and quality of the coating.

2. The method of claim 1 wherein said contiguous areas are disposed within a health care facility for patients with the patients confined within one of said areas with said method being applied to personnel passing through said portal into the area in which the patients are confined.

3. The method of claim 1, wherein sensors for assessing the quality of protection and an estimated antinfection time are disposed within the antinfection zone and connections between said sensors and a computer system.

4. The method of claim 1 wherein said high persistence antiseptic coating comprises an inert water carrier plus halogens.

5. The method of claim 1 wherein said certain exposed body parts of said personnel are subjected to said antiseptic skin coating by spraying.

6. The method of claim 5 wherein the sprayed coating matrix of polymers is applied after the exposed body parts are subjected to said antiseptic skin coating.

7. The method of claim 5 wherein said exposed body parts are subjected to the antiseptic skin coating simultaneously with said spraying with said sprayed coating matrix of polymers.

8. The method of claim 5 wherein both the antiseptic skin coating and the matrix of polymers is applied to the skin of said certain exposed body parts by a spray employing multiple and moving controlled nozzles.

9. The method of claim 1 wherein the antinfection spray is applied to the exposed body parts utilizing an electrostatic field between spray nozzles for the antinfection spray and the exposed skin surfaces.

10. The method of claim 1 wherein the antiseptic skin coating and the coating matrix are both applied to said certain exposed body parts by a spray device.

11. The method of claim 10 wherein said spray device further comprises means for evaluating the antiseptic strength of the coatings.

12. The method of claim 1 in which the measuring of the antiseptic strength of the coatings comprises a fluorescent measurement.

13. The method of claim 1 wherein said certain exposed body parts are resprayed and recoated if the measured strength of the coating indicates that the effective time of the antiseptic coating is less than a predetermined criteria.

14. The method of claim 1 in which the halogen is fluorine.

15. The method of claim 14 in which the halogen is in the form of $CaF_2$.

16. The method of claim 15 wherein the high persistence skin coating further comprises organic acids and organic salts.

17. The method of claim 1 wherein the polymers in the sprayed coating matrix have a molecular weight in excess of 40,000, building a sponge-like reservoir for the antiseptic material.

18. The method of claim 1 wherein said certain exposed body parts of the personnel comprise their hands.

19. The method of claim 18 wherein the hands of the personnel are washed before the spray is applied.

20. The method of claim 1 in which the coatings are pressed on the skin and activated by a pressure hot-air blower.

* * * * *